United States Patent [19]

Ogawa et al.

[11] Patent Number: 4,865,593
[45] Date of Patent: Sep. 12, 1989

[54] SPLITTABLE CANNULA

[75] Inventors: Masaki Ogawa; Nobuyoshi Fujiwara, both of Tokyo, Japan

[73] Assignee: Sherwood Medical Company, St. Louis, Mo.

[21] Appl. No.: 210,606

[22] Filed: Jun. 23, 1988

[30] Foreign Application Priority Data

Jun. 25, 1987 [JP] Japan .................................. 62-15848

[51] Int. Cl.$^4$ ............................................. A61M 5/00
[52] U.S. Cl. ................................... 604/264; 604/160
[58] Field of Search ............... 604/160, 164, 280, 166; 128/348.1

[56] References Cited

U.S. PATENT DOCUMENTS

| | | | |
|---|---|---|---|
| Re. 31,855 | 3/1985 | Osborne | 604/161 |
| 3,877,429 | 4/1975 | Rasumoff | 128/214.4 |
| 4,402,685 | 9/1983 | Buhlër et al. | 604/280 |
| 4,581,019 | 4/1986 | Curelaru | 604/164 |
| 4,772,266 | 9/1988 | Groshong | 604/164 |

FOREIGN PATENT DOCUMENTS 2439591  5/1980  France .
8203558 10/1982  PCT Int'l Appl. .
 830376 11/1983  PCT Int'l Appl. .

*Primary Examiner*—Stephen C. Pellegrino
*Attorney, Agent, or Firm*—Stanley N. Garber; Andrew J. Beck; Richard D. Allison

[57] ABSTRACT

A cannula, such as commonly used for introduction of a catheter through the cannula into a body cavity, includes a plastic tube and an adaptor at one end of the tube. For easy removal of the cannula from around the catheter, the tube and adaptor are splittable along two or more longitudinal grooves or induction lines in the tube and adaptor. The induction lines are circumferentially spaced apart by an angle of 45° to 180°. Near the end of the tube opposite the adaptor, the induction lines in the tube are twisted, or extend circumferentially, providing increased stability of the induction lines to minimize premature splitting during manipulation of the cannula.

6 Claims, 1 Drawing Sheet ial lines are twisted with respect to the longitudinal direction in the neighborhood of the open end. The # SPLITTABLE CANNULA

BACKGROUND OF THE INVENTION (1) Field of the Invention

This invention relates to improvements in a readily splittable plastic cannula used for inserting a long catheter into a body cavity such as a blood vessel.

(2) Description of the Prior Art

The usual plastic cannula has a role of securing a guide section for smoothly inserting a long catheter or the like into the body cavity. After the catheter has been inserted, however, it constitutes an abstract in a subsequent operation. For this reason, a plastic cannula which can be removed by splitting after the insertion of the catheter or the like has been developed.

Such readily splittable plastic cannula are disclosed in Japanese Utility Model Registration 51-1661, Japanese Patent Laid-Open 56-11069 and Japanese Patent Laid-Open 59-91968. These disclosed structures are capable of being split or divided in the longitudinal direction so that they can be removed from the body cavity by pulling them after their role of guiding a catheter is over.

SUMMARY OF THE INVENTION

In the prior art structure, the cannula can be removed from the body cavity by pulling it after its role is over. With this structure, however, the cannula is liable to be cracked along its split induction line before it is set in a stable state for insertion into the body tissue, or it is liable to be cracked along the split induction line from its open end during storage or transport. Whether the cannula is cracked cannot be certified from the appearance unless the cannula is checked by pushing its end with a hand, and it is often the case that a crack of the cannula is found from the pain of the patient when the cannula is actually used for the patient. In this way, the cracking is a serious problem which has to be solved from the humanity standpoint as well. However, the above problem becomes more serious if the readiness of splitting as a desired function of the cannula is sought, while an intent of solving this problem leads to difficulty of splitting.

The inventors have conducted researches and investigations to find that the above drawback may be solved by the provision of a cannula which consists of a plastic tube having two or more parallel longitudinal split induction lines circumferentially spaced apart by an angle of 45° to 180°, and in which the split induction lines of the tube are twisted with respect to the longitudinal direction for its portion in the neighborhood of its open end.

Further, it has been found that such a cannula can be produced as perfect industrial product by forming it such that it comprises a plastic tube having split induction lines and a plastic adapter integral with one end of a stem portion of the tube, connecting split induction lines on the outer periphery of the adapter to two of the split induction lines of the tube and forming split induction grooves for promoting the splitting along the split induction lines.

DESCRIPTION OF THE PREFERRED EMBODIMENT

Figure 1:
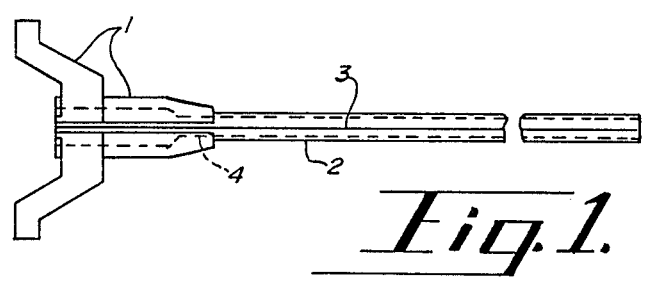
FIG. 1 is a front view showing a readily splittable plastic cannula.

The range, in which the split induction lines of the tube are twisted with respect to the longitudinal direction, is suitably 0.3 to 3.0 mm from the open end, and the pitch of twisting is suitably 6 mm per rotation.

Further, the adapter suitably includes two grips formed integrally at positions spaced apart by an equal distance from the two split induction grooves. The split induction grooves suitably have a V-like, U-like, semicircular or channel-like sectional profile, have an increased depth from the end of the adapter coupled to the tube to the stem end and be such that the stem end and neighborhood thereof constitute a comparatively high mechanical strength adapter portion. Further suitably, the adapter has a tube stem open section capable of snugly fitting with respect to an administration syringe.

The split induction lines of the plastic tube of the cannula are twisted with respect to the longitudinal direction in the neighborhood of the open end in order to prevent cracks from being generated and proceed from the open end along the split induction lines. The range, in which the twist is formed, is 0.3 to 3.0 mm, preferably 1.0 to 2.0 mm, from the end. If this range is exceeded, high resistance is offered against a splitting effort from a stem portion as well, so that the splitting property is deteriorated. If the range is less than 0.3 mm, it is no longer possible to expect an effect of prevention of cracks from being generated and proceeding from the open end along the split induction lines. In addition, it is difficult to manufacture industrially uniform produce.

The extent, to which the split induction lines of the tube are twisted with respect to the longitudinal lines, is suitably 6 mm per rotation or below. If the extent is less than this value, it is impossible to expect the effect of prevention of cracks from being generated and proceeding from the open end along the split induction lines. If the pitch is less than 1 mm per rotation, the splitting of the end portion of the tube becomes very difficult.

According to the invention, the split induction lines should be circumferentially spaced apart by an angle of 45° to 180°. If the angle is less than 45°, the split portion of the tube strongly embraces the inserted catheter, so that it becomes very difficult to remove the cannula. More effective angle range for readily splitting is 100° to 180°. If it is desired to let the catheter be left in one split portion of the cannula so as to reduce the shock when splitting the cannula and thus reduce damage to the patient's structure, the angle range is suitably 100° to 150°.

If only a single split induction line is provided, a great shock is given to the inserted catheter, imposing great burden on the patient's structure. In addition, in this case, the significance of combination of the adapter according to the invention is lost. It is possible to provide three or more split induction lines. However, in this case, difficulties are encountered in the industrial manufacturing process. For the above reasons, most usually two split induction lines are provided in actual use.

According to the invention, the adapter is suitably provided which has its outer surface formed with split induction grooves coupled to two of the split induction lines of the tube. This is so in order to promote generation and progress of cracks from the stem end along the split induction lines of the tube. For the same reason, it is better to provide two grips formed integrally such that they project sidewise from positions spaced apart by an equal distance from the split induction lines of the adapter.

EXAMPLE 1

Figure 2:
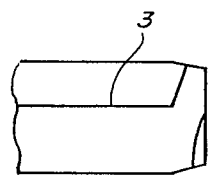
FIG. 2 is an enlarged-scale front view showing an end portion of a readily splittable plastic cannula as Example 1 of the invention.

A hard polyethylene cannula as shown in FIG. 1 was formed, which has two split induction lines circumferentially spaced apart by an angle of 180° and extending parallel to each other in the longitudinal direction, the split induction lines being given a pitch for their length of 1.4 mm from the open end and at a pitch of 1.38 mm per rotation (FIG. 2).

COMPARATIVE EXAMPLE 1

Figure 3:
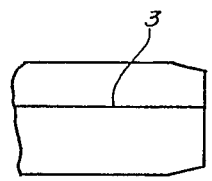
FIG. 3 is an enlarged-scale front view showing an end portion of a prior art readily splittable plastic cannula without any twist of split induction lines. 1 . . . adapter, 2 . . . tube, 3 . . . split induction lines, 4 . . . high frequency weldment.

A cannula was manufactured from the same material as in Example 1 such that it had the same shape but was free from the twist of the split induction lines in the neighborhood of the open end (FIG. 3).

EXAMPLES 2 to 5

Cannula were manufactured from the same material as in Example 1 such that they had the same shape but had different pitches of twist from the open end.

EXAMPLES 7 to 12

Cannula were manufactured from the same material as in Example 1 such that they had the same shape, but the range for which the twist was formed from the open end was different.

EXAMPLES 13 and 14

Cannula were manufactured from polypropylene such that they had respective three and two split induction lines circumferentially spaced apart by 120° and extending parallel to each other in the longitudinal direction, the split induction lines being given a twist for a length of 1.5 mm and having a pitch of 1.82 mm per rotation.

Of 100 products of the above examples, the appearance, readiness of splitting and stability of the open end (examining the state of crack generation by repeating five times an operation of pushing the structure with finger along the split induction lines and then after turning the structure by 90°) results are as shown in Table 1.

As is apparent from Table 1, if the length of twist is less than 0.3 mm, the stability of split induction lines is deteriorated. If the twist length is above 3.0 mm, the appearance and readiness of splitting are deteriorated. Further, if the pitch of twist is above 6.0 mm per rotation, the stability of split induction lines is lower.

As has been shown in the foregoing, according to the invention it is possible to provide a readily splittable plastic cannula which, although difficulty splittable from the distal end, is readily splittable from the stem end, has an end portion which can be smoothly split with the progress of cracking from the stem end, has extremely improved safety, stability and adaptability and can be used for the patient with peace of mind.

TABLE I

| | Length of Twist (mm) | Pitch of Twist (mm/rotation) | Appearance | Tendency to Split | Stability of Open End |
|---|---|---|---|---|---|
| Comparative Example | 1.40 | — | Excellent | Excellent | 11/100 |
| Example 1 | 1.40 | 1.38 | Excellent | Excellent | 0/100 |
| Example 2 | 1.20 | 8.00 | Excellent | Excellent | 1/100 |
| Example 3 | 1.20 | 6.00 | Excellent | Excellent | 0/100 |
| Example 4 | 1.20 | 2.00 | Excellent | Excellent | 0/100 |
| Example 5 | 1.40 | 1.67 | Excellent | Excellent | 0/100 |
| Example 6 | — | — | — | — | — |
| Example 7 | 0.25 | 1.25 | Excellent | Excellent | 1/100 |
| Example 8 | 0.30 | 1.25 | Excellent | Excellent | 0/100 |
| Example 9 | 1.00 | 1.18 | Excellent | Excellent | 0/100 |
| Example 10 | 2.00 | 1.67 | Excellent | Excellent | 0/100 |
| Example 11 | 3.00 | 1.67 | Good | Excellent | 0/100 |
| Example 12 | 4.00 | 1.67 | Good | Good | 0/100 |
| Example 13* | 1.50 | 1.82 | Excellent | Excellent | 0/100 |
| Example 14* | 1.50 | 1.82 | Good** | Excellent | 0/100 |

Note
*designates polypropylene (others made of high density polyethylene)
**cannula was curved

We claim:

1. A readily splittable plastic cannula consisting of a plastic tube having two or more split induction lines circumferentially spaced apart at an angle of 45° to 80° and extending parallel to each other in the longitudinal direction, said split induction lines being twisted with respect to the longitudinal direction in the neighborhood of the open end.

2. The readily splittable plastic cannula according to claim 1, comprising a plastic tube having split induction lines and a plastic adapter made integral with a stem end of said tube, said adapter having a bore communicating with the bore of said tube and having the outer surface formed with split induction lines coupled to two of the split induction lines of said tube and forming split induction grooves.

3. The readily splittable plastic cannula according to claim 1, wherein the length of twist in the longitudinal direction of the split induction lines of said tube is 0.3 to 3.0 mm, preferably 1.0 to 2.0 mm, from the open end.

4. The readily splittable plastic cannula according to claim 1, wherein the pitch of the twist with respect to the longitudinal direction of the split induction lines of said tube is 6 mm per rotation.

5. The readily splittable plastic cannula according to claim 2, wherein said adapter includes two grips integrated and projecting sidewise from positions spaced apart by an equal distance from said two split induction grooves.

6. The readily splittable plastic cannula according to claim 2, wherein said split induction grooves have a V-shaped, U-shaped, semi-circular or channel-shaped sectional profile, said grooves have the depth increased from the end of said adapter connected to said tube to the stem end, and said stem end and neighborhood thereof constitute a comparatively high mechanical strength adapter portion.

* * * * *